(12) United States Patent
Sartor

(10) Patent No.: US 10,952,787 B2
(45) Date of Patent: Mar. 23, 2021

(54) ENERGY-BASED SURGICAL DEVICE AND SYSTEM FACILITATING TISSUE REMOVAL

(71) Applicant: COVIDIEN LP, Mansfield, MA (US)

(72) Inventor: Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 629 days.

(21) Appl. No.: 15/835,427

(22) Filed: Dec. 7, 2017

(65) Prior Publication Data
US 2019/0175255 A1    Jun. 13, 2019

(51) Int. Cl.
| | | |
|---|---|---|
| A61B 18/14 | (2006.01) | |
| A61B 17/28 | (2006.01) | |
| A61B 17/34 | (2006.01) | |
| A61B 18/12 | (2006.01) | |
| A61B 18/00 | (2006.01) | |

(Continued)

(52) U.S. Cl.
CPC ........ *A61B 18/1445* (2013.01); *A61B 17/282* (2013.01); *A61B 17/3417* (2013.01); *A61B 18/1206* (2013.01); *A61B 18/1485* (2013.01); *A61B 2017/00287* (2013.01); *A61B 2017/2808* (2013.01); *A61B 2017/320024* (2013.01); *A61B 2017/3456* (2013.01); *A61B 2018/00077* (2013.01); *A61B 2018/00083* (2013.01); *A61B 2018/00178* (2013.01);
(Continued)

(58) Field of Classification Search
CPC ............................................. A61B 2018/00601
See application file for complete search history.

(56) References Cited

U.S. PATENT DOCUMENTS

| | | |
|---|---|---|
| 5,403,276 A | 4/1995 | Schechter et al. |
| 5,443,472 A | 8/1995 | Li |

(Continued)

FOREIGN PATENT DOCUMENTS

| | | |
|---|---|---|
| EP | 806183 A1 | 11/1997 |
| GB | 2327350 A | 1/1999 |

(Continued)

OTHER PUBLICATIONS

U.S. Appl. No. 14/325,590, filed Jul. 8, 2014, inventor: Sartor.
Extended European Search Report issued in corresponding European Application No. 18210678.1 dated May 2, 2019, 8 pages.

*Primary Examiner* — Ronald Hupczey, Jr.
(74) *Attorney, Agent, or Firm* — Carter, DeLuca & Farrell LLP

(57) ABSTRACT

An energy-based surgical device includes an elongated outer tube having a distal overhang, a proximal hub, a distal cutting member, and a flat spring. The distal cutting member has a U-shaped cutting edge and defines a mouth with the distal overhang extending therethrough. The flat spring includes a first portion extending distally along an exterior surface of the elongated outer tube and the distal overhang, a second portion extending from the first portion and bent over a free distal end of the distal overhang, and a third portion extending from the second portion proximally through the mouth of the distal cutting member and into the lumen of the elongated outer tube and traverses a majority of a diameter thereof. The distal cutting member and flat spring are adapted to connect to a source for electrosurgical energy for conducting bipolar energy through tissue disposed therebetween to cut tissue.

18 Claims, 11 Drawing Sheets

(51) Int. Cl.
*A61B 17/32* (2006.01)
*A61B 18/16* (2006.01)
*A61B 17/00* (2006.01)

(52) U.S. Cl.
CPC .............. *A61B 2018/00601* (2013.01); *A61B 2018/126* (2013.01); *A61B 2018/1412* (2013.01); *A61B 2018/162* (2013.01)

(56) References Cited

U.S. PATENT DOCUMENTS

| | | | |
|---|---|---|---|
| 5,520,634 | A | 5/1996 | Fox et al. |
| 5,569,284 | A | 10/1996 | Young et al. |
| 5,618,296 | A | 4/1997 | Sorensen et al. |
| 5,669,927 | A | 9/1997 | Boebel et al. |
| 5,746,760 | A | 5/1998 | Humphrey, Jr. |
| 5,916,198 | A * | 6/1999 | Dillow ............... A61B 17/3498 604/167.04 |
| 6,039,748 | A | 3/2000 | Savage et al. |
| 6,045,566 | A | 4/2000 | Pagedas |
| 6,074,386 | A | 6/2000 | Goble et al. |
| 6,110,127 | A * | 8/2000 | Suzuki .................. A61B 10/06 600/564 |
| 6,162,235 | A | 12/2000 | Vaitekunas |
| 6,468,228 | B1 | 10/2002 | Topel et al. |
| D535,748 | S | 1/2007 | Wolf |
| 7,156,839 | B2 | 1/2007 | Bayer et al. |
| 7,232,439 | B2 | 6/2007 | Ciarrocca |
| 7,850,684 | B2 | 12/2010 | Marshall et al. |
| 7,896,877 | B2 | 3/2011 | Hall et al. |
| 8,025,656 | B2 | 9/2011 | Gruber et al. |
| 8,100,928 | B2 | 1/2012 | Nohilly et al. |
| 8,152,820 | B2 | 4/2012 | Mohamed et al. |
| 8,308,746 | B2 | 11/2012 | Pravong et al. |
| 8,343,148 | B2 | 1/2013 | Fleming et al. |
| 8,608,764 | B2 | 12/2013 | Ambardekar |
| 8,652,156 | B2 | 2/2014 | Holdgate et al. |
| 8,900,230 | B2 | 12/2014 | Jenkins et al. |
| 9,066,724 | B2 | 6/2015 | Jenkins |
| 9,089,337 | B2 | 7/2015 | Batchelor et al. |
| 9,615,876 | B2 | 4/2017 | Jenkins et al. |
| 9,649,147 | B2 | 5/2017 | Gilbert et al. |
| 9,913,653 | B2 | 3/2018 | Sartor et al. |
| 2005/0261676 | A1 | 11/2005 | Hall et al. |
| 2006/0089527 | A1 | 4/2006 | Doll et al. |
| 2008/0039880 | A1 | 2/2008 | Nohilly et al. |
| 2008/0039883 | A1 | 2/2008 | Nohilly |
| 2008/0058846 | A1 | 3/2008 | Vosough |
| 2008/0065129 | A1 | 3/2008 | Batchelor et al. |
| 2008/0103412 | A1 | 5/2008 | Chin |
| 2008/0135780 | A1 | 6/2008 | Giering et al. |
| 2008/0255597 | A1 * | 10/2008 | Pravong ........... A61B 17/32002 606/169 |
| 2009/0292281 | A1 | 11/2009 | Fleming et al. |
| 2010/0305566 | A1 | 12/2010 | Rosenblatt et al. |
| 2011/0184409 | A1 | 7/2011 | Jenkins et al. |
| 2011/0257651 | A1 | 10/2011 | Jenkins |
| 2011/0264129 | A1 | 10/2011 | Holdgate et al. |
| 2012/0016399 | A1 | 1/2012 | Poulsen |
| 2012/0078038 | A1 | 3/2012 | Sahney et al. |
| 2013/0090642 | A1 | 4/2013 | Shadduck et al. |
| 2013/0123797 | A1 | 5/2013 | Livneh |
| 2013/0218186 | A1 | 8/2013 | Dubois et al. |
| 2015/0018815 | A1 * | 1/2015 | Sartor .............. A61B 17/32002 606/39 |
| 2015/0057660 | A1 * | 2/2015 | Jenkins ................ A61B 18/082 606/48 |

FOREIGN PATENT DOCUMENTS

| | | |
|---|---|---|
| GB | 2327351 A | 1/1999 |
| GB | 2436065 A | 9/2007 |
| WO | 9724074 A1 | 7/1997 |
| WO | 2009141579 A1 | 11/2009 |
| WO | 2014/123571 A1 | 8/2014 |

* cited by examiner

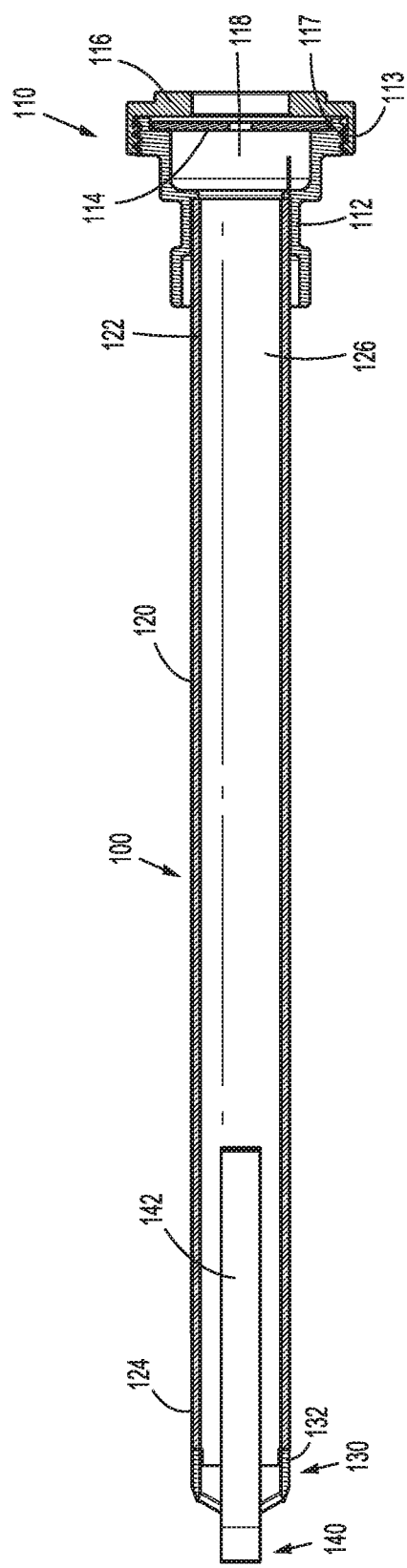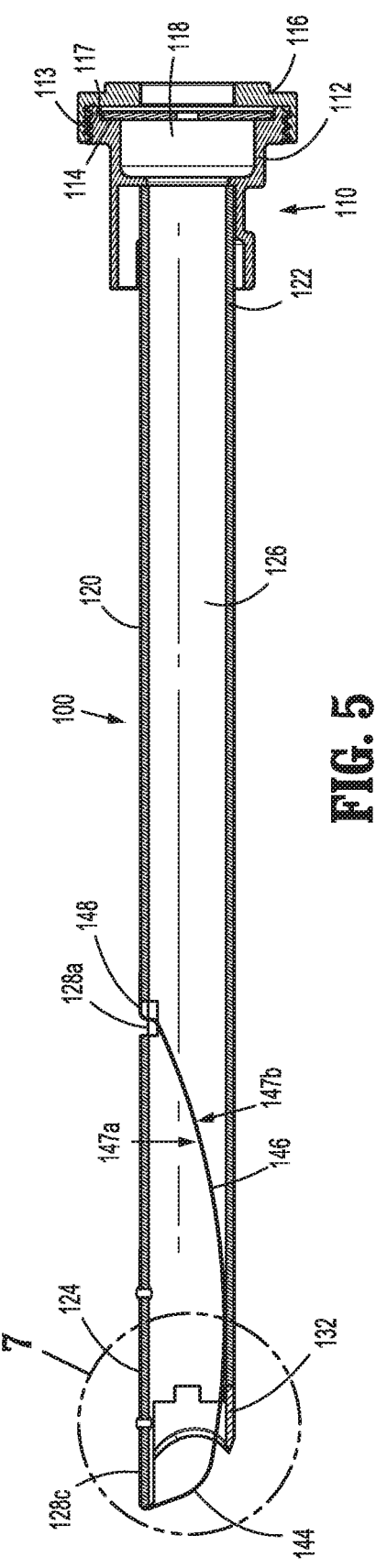
FIG. 4
FIG. 5

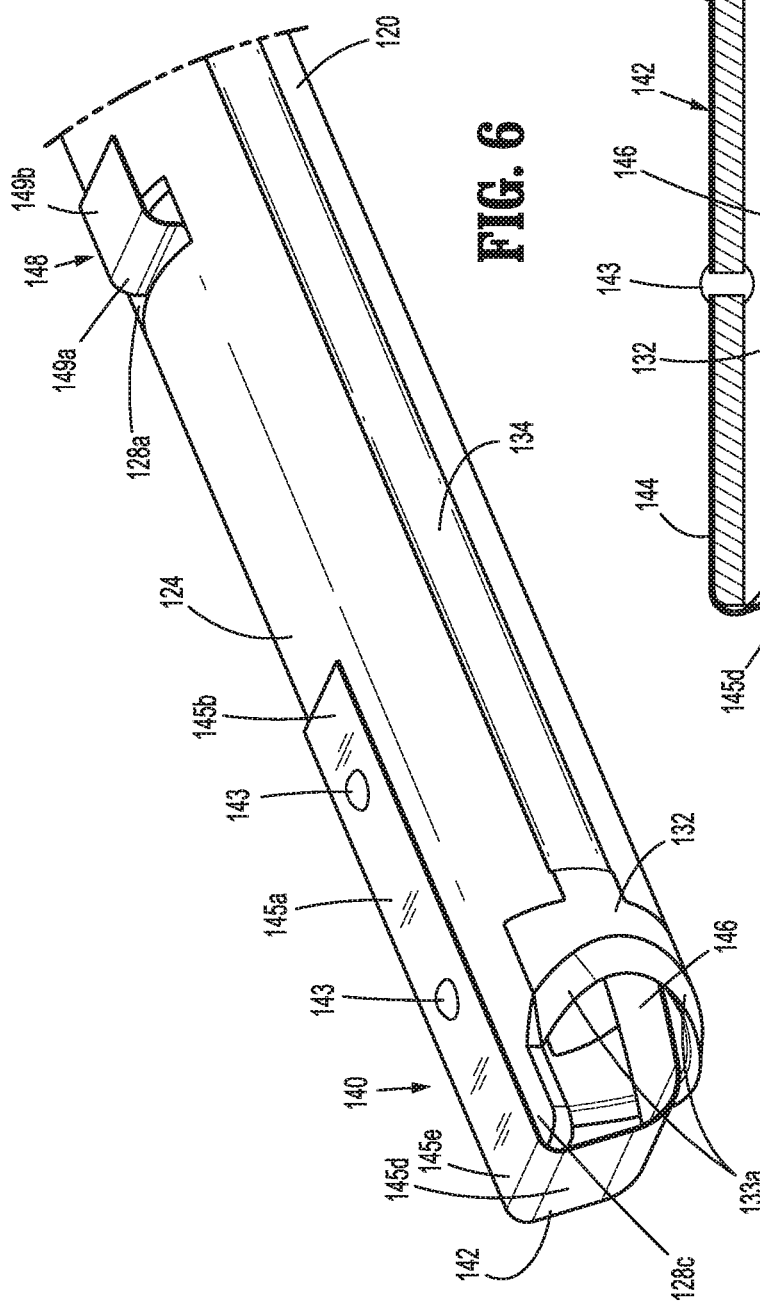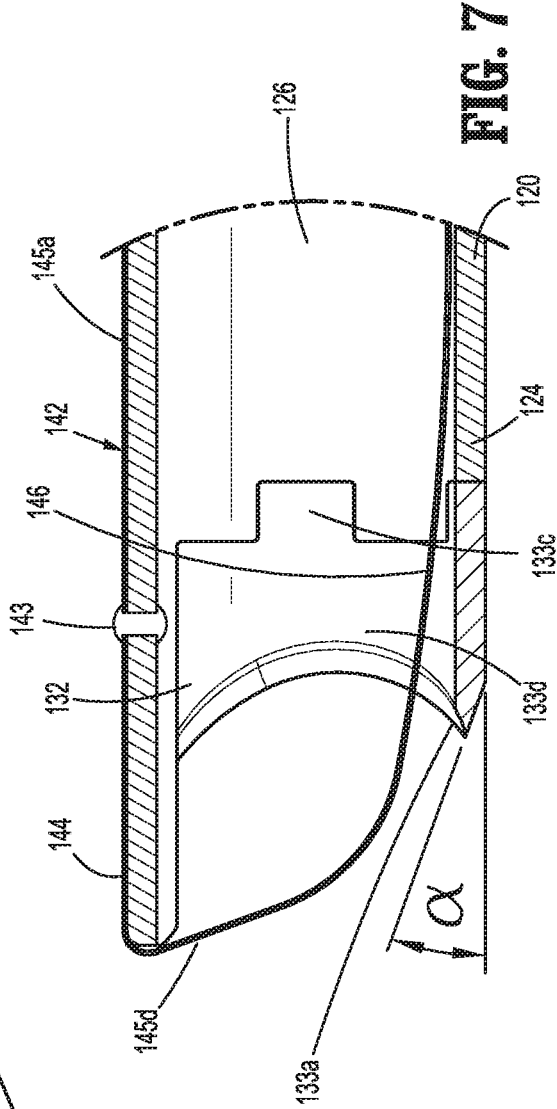

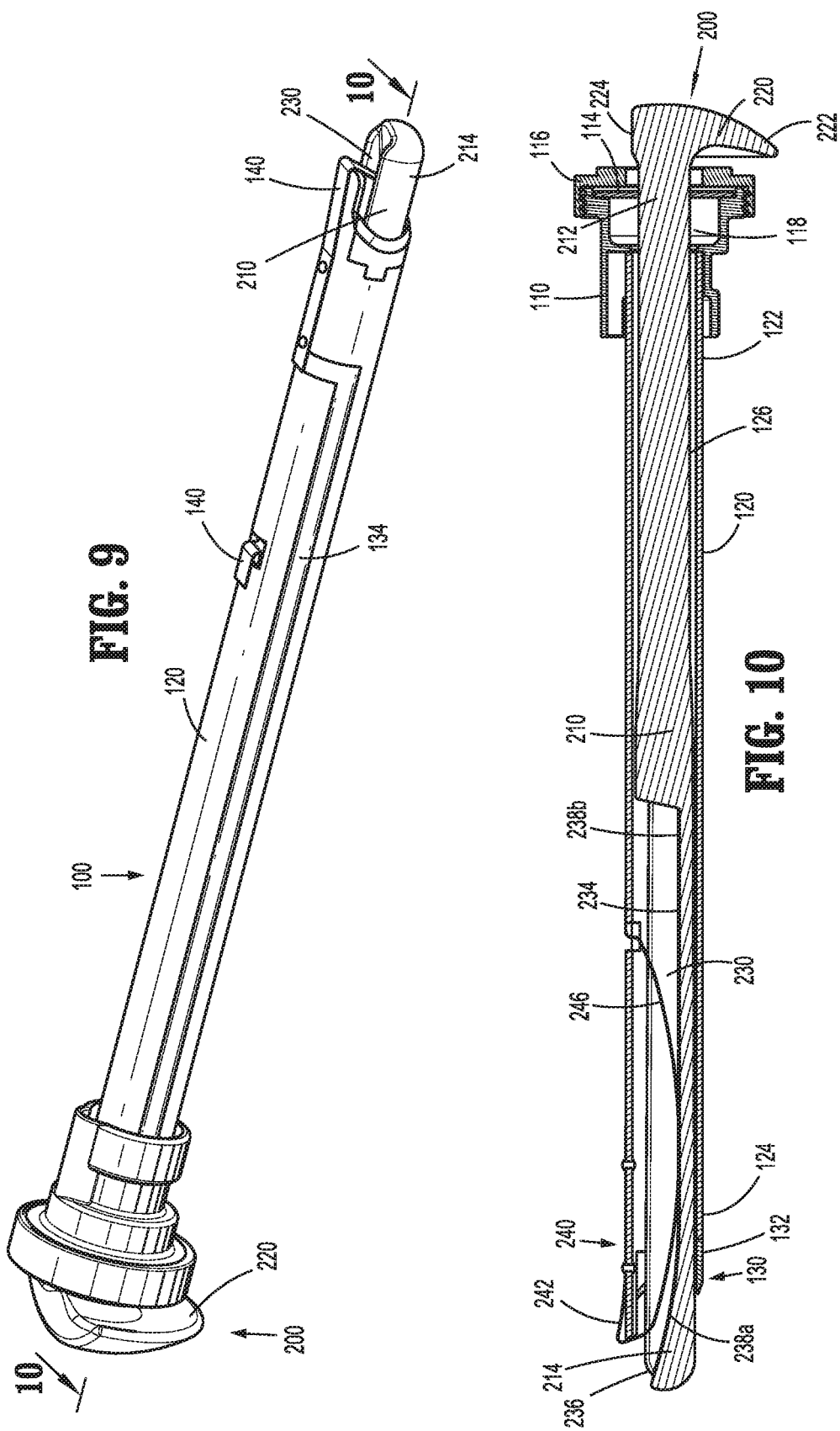

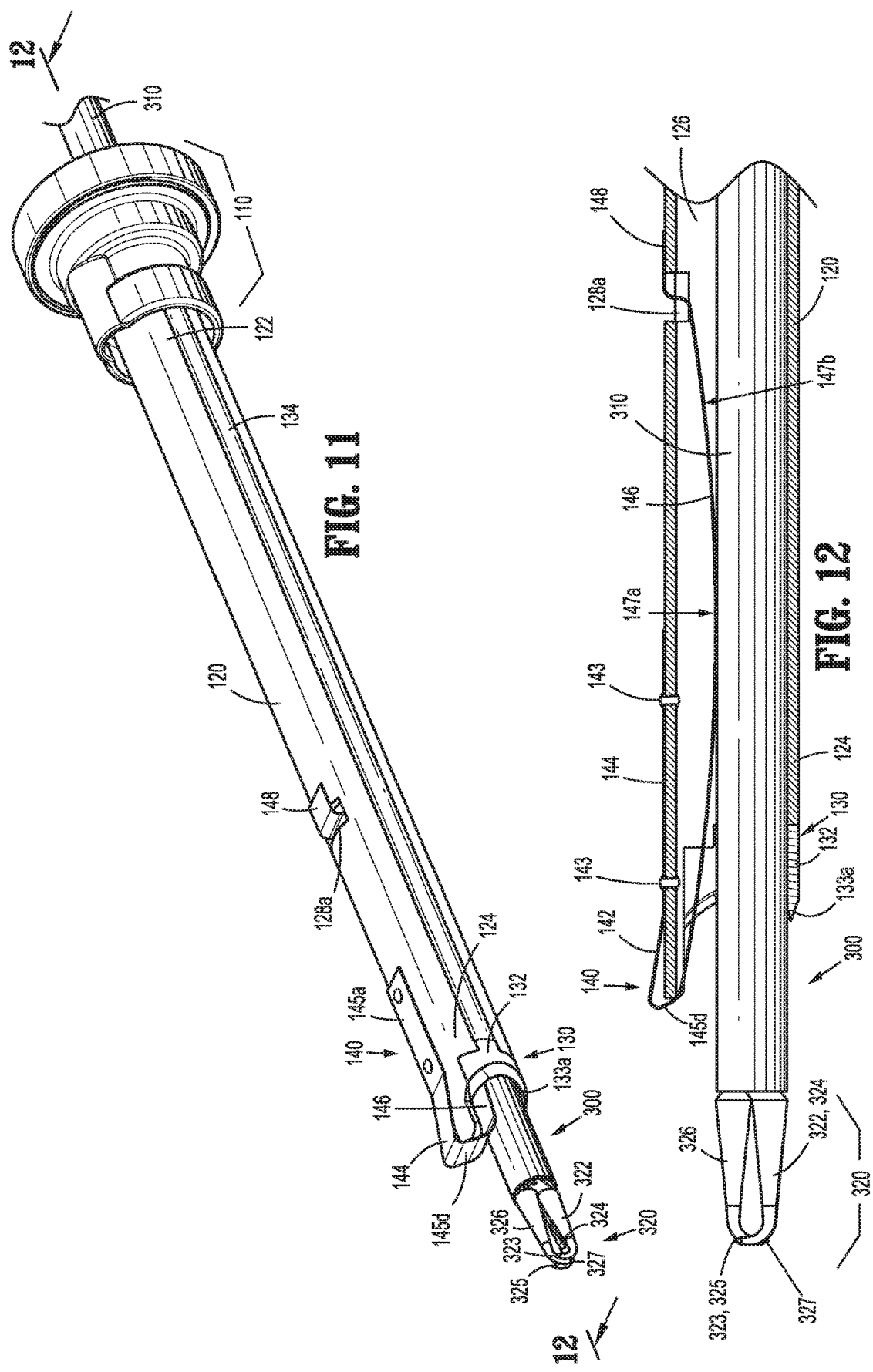

ENERGY-BASED SURGICAL DEVICE AND SYSTEM FACILITATING TISSUE REMOVAL

BACKGROUND

Technical Field

The present disclosure relates to tissue removal and, more particularly, to an energy-based surgical device and system facilitating breakdown of tissue to enable removal from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to removal of large tissues. As such, tissues that are deemed too large for intact removal are broken down into a plurality of smaller pieces to enable removal from the internal body cavity. With respect to breaking down such tissues, there is the challenge of doing so within confines of the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an energy-based surgical device including an elongated outer tube, a proximal hub, a distal cutting member, and a flat spring. The elongated outer tube defines a distal end portion, a proximal end portion, and a lumen extending longitudinally therethrough. The elongated outer tube further includes a distal overhang extending distally therefrom. The proximal hub is disposed at the proximal end portion of the elongated outer tube. The distal cutting member is disposed at the distal end of the elongated outer tube, has a U-shaped cutting edge, and defines a mouth. The distal overhang extends through the mouth. The flat spring is aligned with the distal overhang and includes: a first portion extending distally along an exterior surface of the elongated outer tube and the distal overhang, a second portion extending from the first portion and bent over a free distal end of the distal overhang, and a third portion extending from the second portion proximally through the mouth of the distal cutting member and into the lumen of the elongated outer tube. The distal cutting member and the flat spring are adapted to connect to a source for electrosurgical energy for conducting bipolar energy through tissue disposed therebetween to cut tissue.

In an aspect of the present disclosure, the third portion of the flat spring traverses a majority of a diameter of the lumen of the elongated outer tube; a substantial portion of the diameter of the lumen of the elongated outer tube; or an entirety of the diameter of the lumen of the elongated outer tube.

In another aspect of the present disclosure, the third portion of the flat spring is resiliently flexible to permit insertion of an instrument through the elongated outer tube.

In still another aspect of the present disclosure, the flat spring includes a fourth portion extending from the third portion. The forth portion extends from the lumen of the elongated outer tube, through a slot defined within the elongated outer tube, to an exterior of the elongated outer tube.

In yet another aspect of the present disclosure, the second portion of the flat spring includes a face covering a portion of the lumen and oriented in a distally-facing direction.

In another aspect of the present disclosure, the first portion of the flat spring is engaged to the exterior surface of the elongated outer tube via at least one rivet.

In still yet another aspect of the present disclosure, the U-shaped cutting edge of the distal cutting member defines an edge angle from about 10 degrees to about 30 degrees.

In another aspect of the present disclosure, uprights of the U-shaped cutting edge are concave.

In still another aspect of the present disclosure, the proximal hub includes a seal disposed therein and configured to sealingly engage an instrument inserted therethrough.

In yet another aspect of the present disclosure, one or more flat conductors extending along the exterior surface of the elongated outer tube. The one or more flat conductors are electrically coupled to the distal cutting member and adapted to connect to a source of electrosurgical energy to supply electrosurgical energy to the distal cutting member.

A surgical system provided in accordance with aspects of the present disclosure includes an energy-based surgical device and a tenaculum. The energy-based surgical device includes an elongated outer tube defining a distal end portion, a proximal end portion, and a lumen extending longitudinally therethrough. The energy-based surgical device further includes a proximal hub disposed at the proximal end portion of the elongated outer tube, and a distal cutting member disposed at the distal end of the elongated outer tube. The distal cutting member is adapted to connect to a source for electrosurgical energy for applying electrosurgical energy to tissue. The energy-based surgical device further includes a resiliently flexible flat spring including a portion extending proximally into the lumen of the elongated outer tube. The portion of the flat spring defines an arcuate configuration.

The tenaculum includes an elongated shaft and an end effector assembly disposed at a distal end portion of the elongated shaft. The elongated shaft is formed at least partially from an electrically-conductive material adapted to connect to a source for electrosurgical energy. The tenaculum is configured for insertion through the lumen of the elongated outer tube whereby the elongated shaft of the tenaculum displaces the portion of the flat spring such that the portion of the flat spring is biased into contact with the elongated shaft of the tenaculum to establish electrical continuity therebetween to define a return path for the electrosurgical energy.

In an aspect of the present disclosure, the end effector assembly of the tenaculum incudes at least two pivotable jaw members configured to pivot relative to one another to grasp tissue.

In another aspect of the present disclosure, the distal cutting member of the energy-based surgical device includes a U-shaped cutting edge defining a mouth having the flat spring extending therethrough.

In another aspect of the present disclosure, the flat spring extends proximally along an exterior surface of the elongated outer tube and bends around the distal end portion of the elongated outer tube before extending proximally into the lumen of the elongated outer tube.

In yet another aspect of the present disclosure, the portion of the flat spring traverses a majority of a diameter of the lumen of the elongated outer tube; a substantial portion of the diameter of the lumen of the elongated outer tube; or an entirety of the diameter of the lumen of the elongated outer tube.

In still another aspect of the present disclosure, the proximal hub includes a seal disposed therein configured to sealingly engage the elongated shaft of the tenaculum when the tenaculum is inserted through the lumen of the elongated outer tube.

In still yet another aspect of the present disclosure, the system further includes an obturator configured for insertion through the lumen of the elongated outer tube. In such aspects, the obturator may define a channel configured to at least partially receive the portion of the flat spring therein when the obturator is inserted through the lumen of the elongated outer tube.

Another energy-based surgical device provided in accordance with aspects of the present disclosure includes an elongated outer tube defining a distal end portion, a proximal end portion, and a lumen extending longitudinally therethrough. The elongated outer tube includes a distal overhang extending distally therefrom. The device further includes a distal cutting member disposed at the distal end of the elongated outer tube that is non-continuous about the distal end portion of the outer tube, has a U-shaped cutting edge, and defines a mouth. The distal overhang extends through the mouth. A flat spring of the device is aligned with the distal overhang and includes a first portion extending from the distal overhang, through the mouth of the distal cutting member, and into the lumen of the elongated outer tube. A portion of the flat spring traverses a majority of a diameter of the lumen of the elongated outer tube. The distal cutting member and the flat spring are adapted to connect to a source for electrosurgical energy for conducting bipolar energy through tissue disposed therebetween to cut tissue.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and:

FIG. 4 is a longitudinal, cross-sectional view of the energy-based surgical device of FIG. 1 taken along section line 4-4 of FIG. 1;

FIG. 5 is a longitudinal, cross-sectional view of the energy-based surgical device of FIG. 1 taken along section line 5-5 of FIG. 1;

FIG. 6 is an enlarged, perspective view of the area of detail indicated as "6" in FIG. 2;

FIG. 7 is an enlarged, longitudinal, cross-sectional view of the area of detail indicated as "7" in FIG. 5;

FIG. 9 is a side, perspective view of the energy-based surgical device of FIG. 1 including the obturator of FIG. 2 inserted therethrough;

FIG. 10 is a longitudinal, cross-sectional view taken along section line 10-10 of FIG. 9;

FIG. 11 is a side, perspective view of the energy-based surgical device of FIG. 1 including the tenaculum of FIG. 2 inserted therethrough;

FIG. 12 is a distal portion of a longitudinal, cross-sectional view taken along section line 12-12 of FIG. 11.

DETAILED DESCRIPTION

The present disclosure provides an energy-based surgical device and system facilitating breakdown of tissue within an internal body cavity to enable removal from the internal body cavity.

Figure 1:
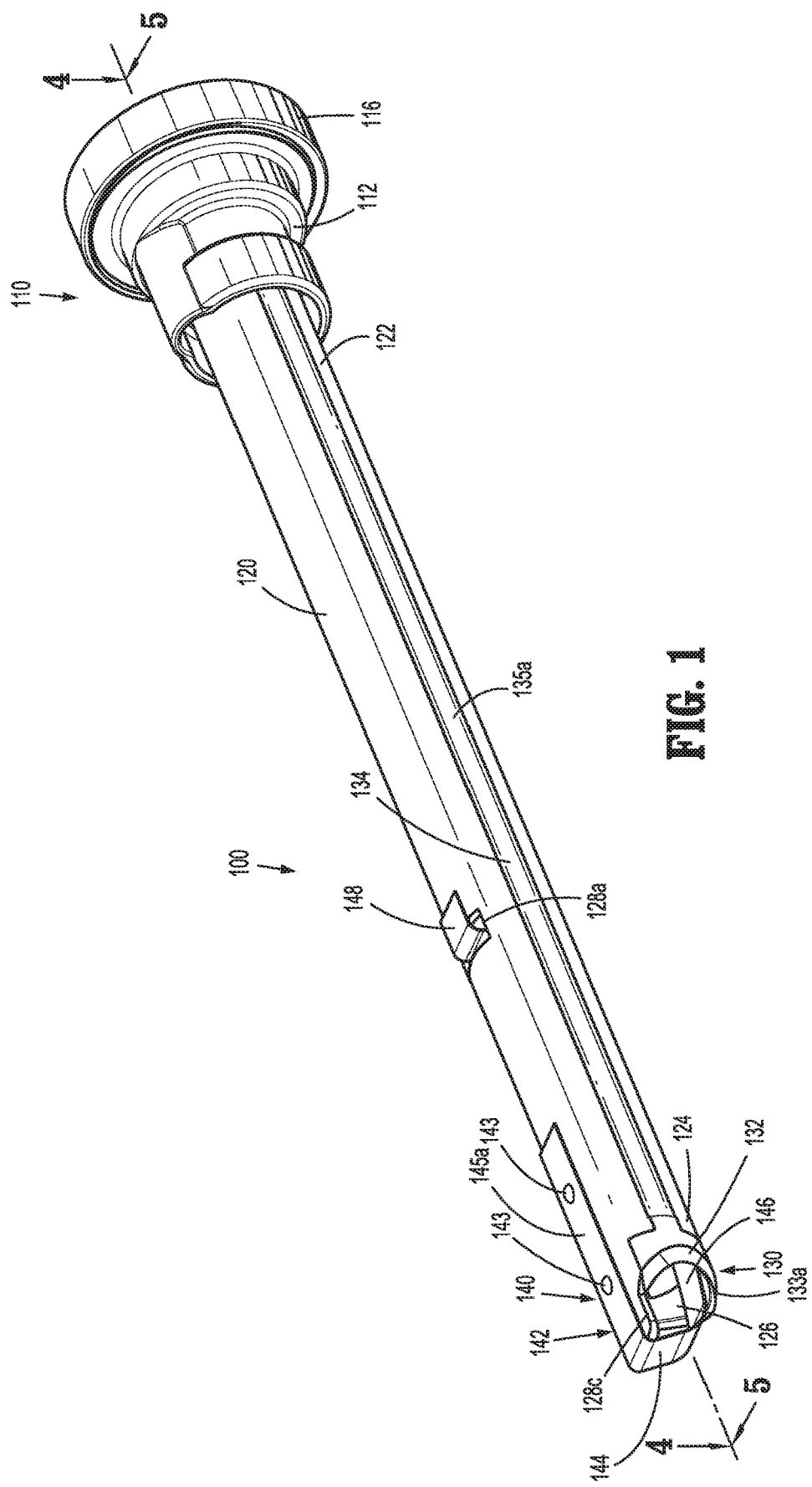
FIG. 1 is a side, perspective view of an energy-based surgical device provided in accordance with the present disclosure.

Turning to FIG. 1, an energy-based surgical device 100 provided in accordance with the present disclosure is shown generally including a proximal hub 110, an elongated outer tube 120, an active electrode assembly 130, and a return electrode assembly 140. Energy-based surgical device 100 is described in detail below. With additional reference to FIG. 2, energy-based surgical device 100, together with obturator 200 and tenaculum 300, provide a surgical system 1000 configured to facilitating breakdown of tissue within an internal body cavity to enable removal from the internal body cavity. Obturator 200 and tenaculum 300 are also described in detail below.

Figure 2:
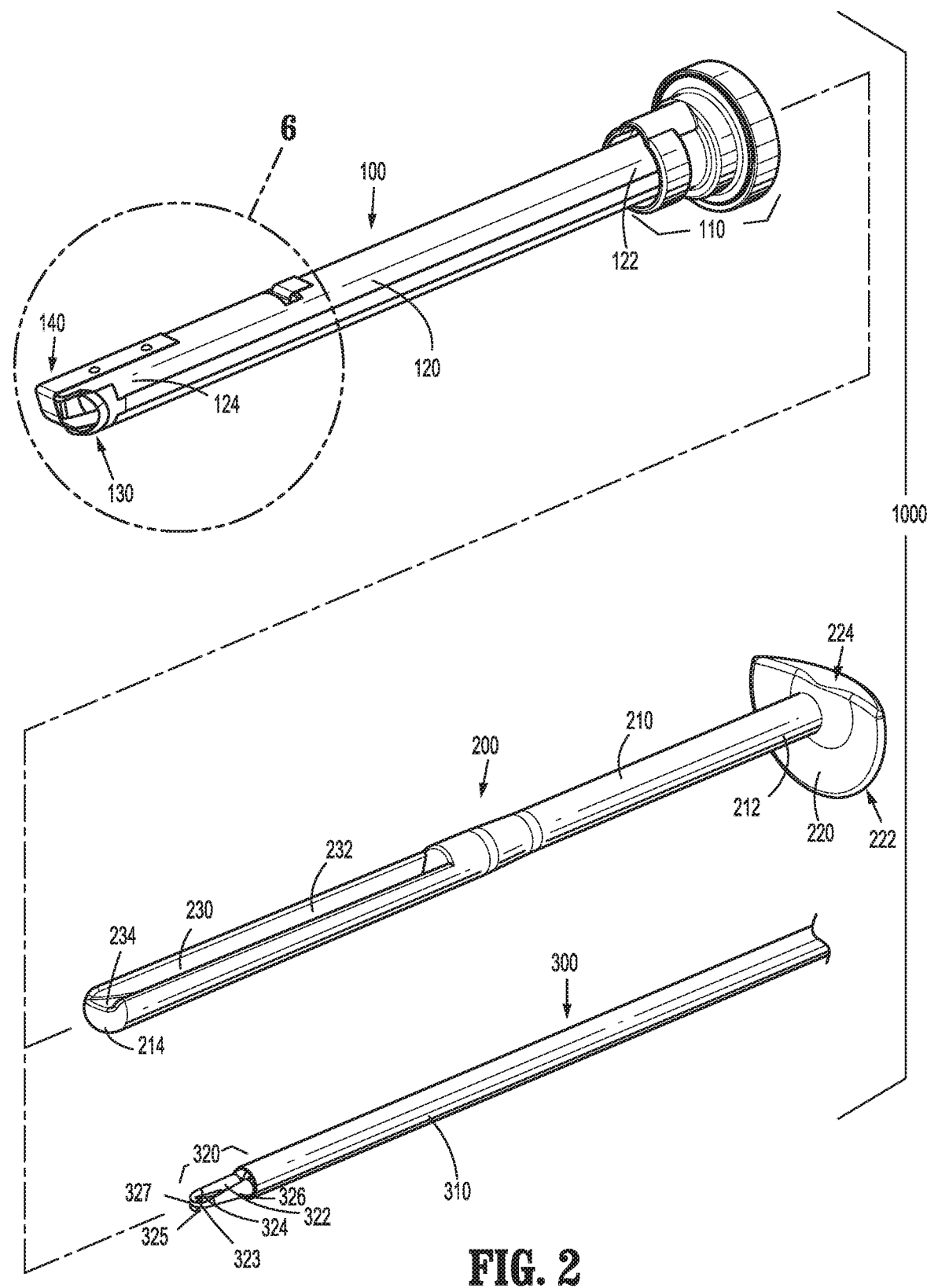
FIG. 2 is an exploded, perspective view of a system provided in accordance with the present disclosure including the energy-based surgical device of FIG. 1, an obturator, and a tenaculum.
Figure 3:
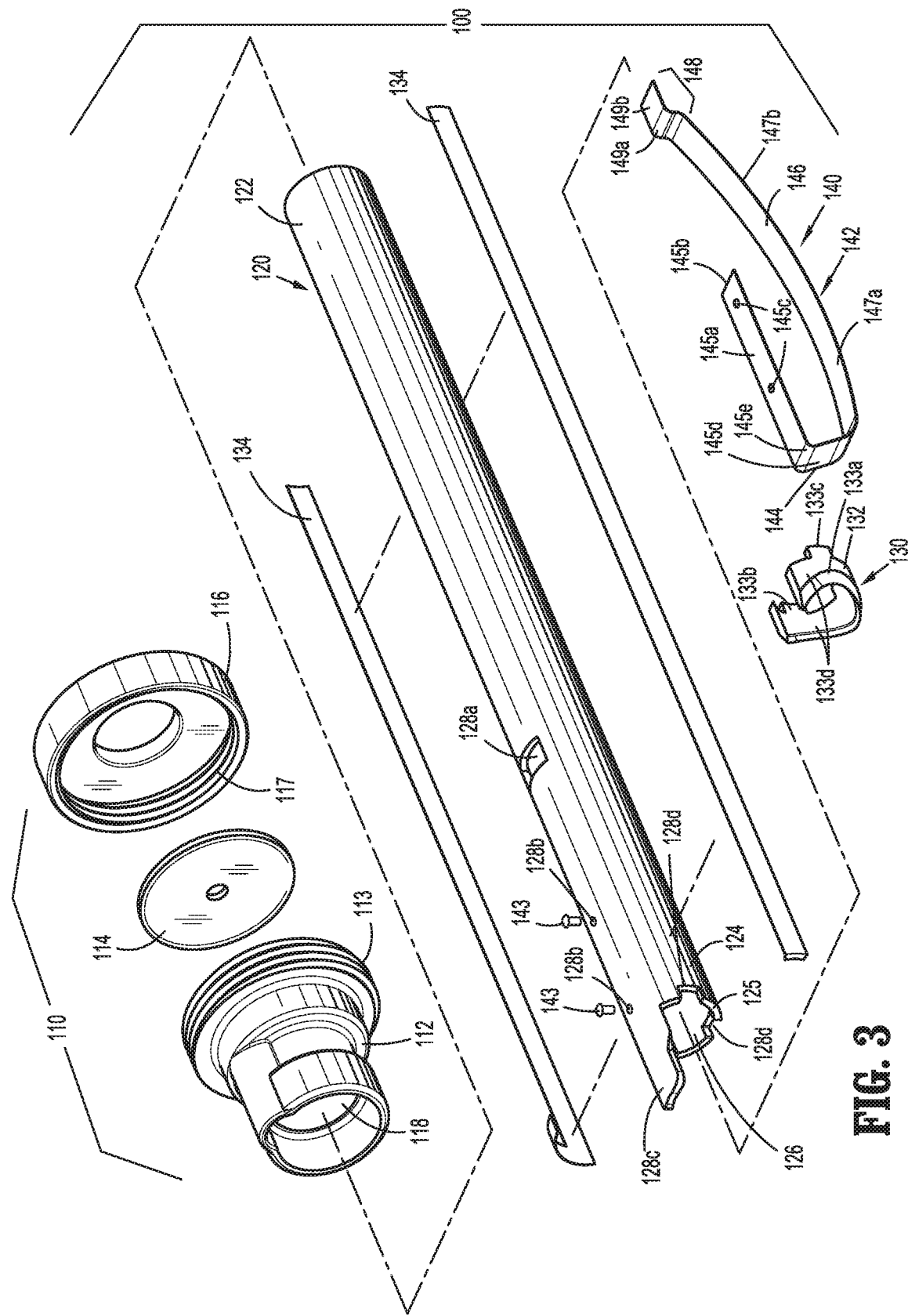
FIG. 3 is an exploded, perspective view of the energy-based surgical device of FIG. 1.
Figure 8:
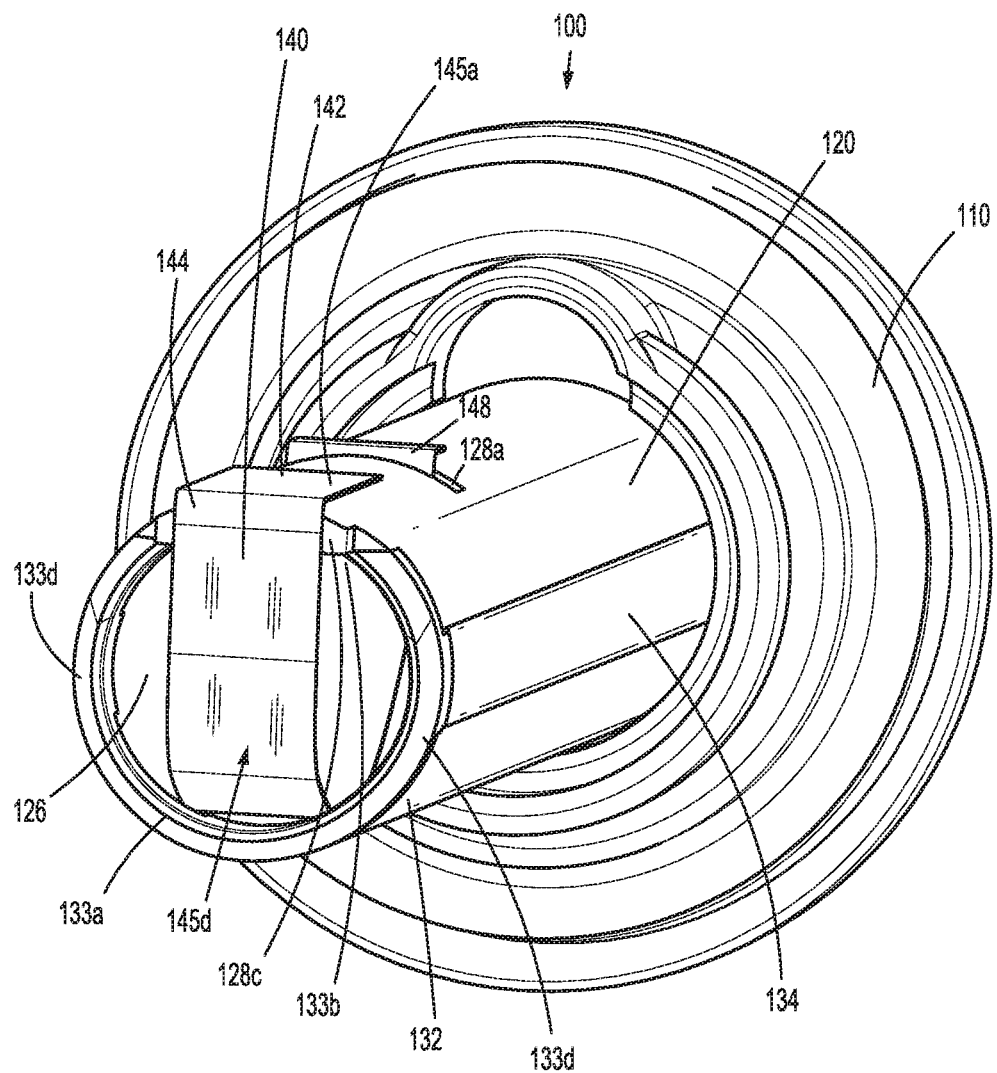
FIG. 8 is an enlarged, front, perspective view of the energy-based surgical device of FIG. 1.

Continuing with reference to FIGS. 1 and 2, surgical system 1000 is configured to connect to a source of bipolar electrosurgical energy, e.g., a bipolar electrosurgical generator (not shown). More specifically, the electrosurgical generator is configured to connect to active electrode assembly 130 of energy-based surgical device 100 to supply electrosurgical energy thereto such that, upon activation, active electrode assembly 130 functions as the active electrode of surgical system 1000. Tenaculum 300 is configured to couple return electrode assembly 140 of energy-based surgical device 100 to the electrosurgical generator such that, upon activation, return electrode assembly 140 functions as the return electrode of surgical system 1000. Activation may be provided by way of a footswitch (not shown), handswitch (not shown) disposed on energy-based surgical device 100 or tenaculum 300, or other suitable activator (not shown).

Referring to FIG. 2, obturator 200 includes an elongated shaft 210 configured for insertion through elongated outer tube 120 of energy-based surgical device 100. Elongated shaft 210 defines a proximal end portion 212 and a distal end portion 214. Obturator 200 further includes a proximal collar 220 disposed at proximal end portion 212 of elongated shaft 210 and configured to facilitate manipulation of obturator 200. Proximal collar 220 also functions as a stop, abutting or otherwise interfering with proximal hub 110 of energy-based surgical device 100 upon full insertion of obturator 200 therethrough to define the fully-inserted position of obturator 200. Distal end portion 214 of elongated shaft 210 defines a blunt, e.g., rounded, configuration to enable atraumatic insertion of obturator 200 and energy-based surgical device 100 through or into any instrumentation and/or through tissue and into an internal body cavity. Elongated shaft 210 defines a length such that, with obturator 200 disposed in the fully-inserted position within energy-based surgical device 100, proximal collar 220 of obturator 200 abuts or is disposed in close proximity to proximal hub 110 of energy-based surgical device 100 (see FIGS. 9 and 10) and distal end portion 214 of obturator 200 protrudes distally from energy-based surgical device 100 (see FIGS. 9 and 10).

With additional reference to FIGS. 9 and 10, obturator 200 further includes a channel 230 defined within elongated shaft 210 and extending proximally from distal end portion 214 thereof. Channel 230 is defined by a pair of opposed side walls 232 (only one of which is visible in FIG. 2) interconnected by a base 234 recessed relative to the exterior surface of elongated shaft 210. Channel 230 further includes an open distal mouth 236. Base 234 of channel 230 includes a distal portion 238a and a body portion 238b extending proximally from distal portion 238a. Distal portion 238a defines a ramped or arced configuration, while body portion 238b defines a generally flat configuration. Distal portion 238a is configured such that channel 230 is increasingly deepened along distal portion 238a in the distal-to-proximal direction from open distal mouth 236 to body portion 238b. Channel 230 defines a generally constant depth along the length of body portion 238b. As detailed below, channel 230 is configured to receive a portion of return electrode assembly 140 of energy-based surgical device 100 to enable insertion of obturator 200 through energy-based surgical device 100 to the fully-inserted position.

Proximal collar 220 of obturator 200 defines a larger radial dimension as compared to elongated shaft 210 so as to facilitate grasping of proximal collar 220 to manipulate obturator 200, e.g., to insert or remove obturator 200 from energy-based surgical device 100. Proximal collar 220 defines a U-shaped outline wherein the outer edge of proximal collar 220 is defined by a radiused edge 222 and a flat edge 224. Flat edge 224 and channel 230 are oriented relative to one another to face a similar direction. As such, by visualizing or feeling flat edge 224 of proximal collar 220, the orientation of channel 230 can be readily determined. Such a configuration facilitates alignment of channel 230 with return electrode assembly 140 of energy-based surgical device 100 to facilitate insertion of obturator 200 into energy-based surgical device 100.

Referring back to FIG. 2, tenaculum 300 includes an elongated shaft 310 configured for insertion through elongated outer tube 120 of energy-based surgical device 100, and an end effector assembly 320 disposed at a distal end portion of elongated shaft 310. Tenaculum 300 may include an actuator (not shown), e.g., a plunger, movable handle, trigger, etc., at a proximal end portion thereof (not shown) to enable actuation of end effector assembly 320 from a proximal end portion of tenaculum 300.

With additional reference to FIGS. 11 and 12, elongated shaft 310 defines a length such that, with tenaculum 300 inserted through energy-based surgical device 100, end effector assembly 320 extends distally from energy-based surgical device 100 while the actuator of tenaculum 300 remains proximally-disposed relative to energy-based surgical device 100. Elongated shaft 310 is formed at least partially from an electrically-conductive material and is configured to connect to the electrosurgical generator, e.g., via one or more lead wires extending through an electrosurgical cable (not shown). Return electrode assembly 140 of energy-based surgical device 100 is biased into contact with the exterior surface of elongated shaft 310 when tenaculum 300 is inserted through energy-based surgical device 100, as detailed below, such that return electrode assembly 140 and elongated shaft 310 are electrically coupled with one another. As such, with return electrode assembly 140 electrically coupled to elongated shaft 310 and elongated shaft 310 connected to the electrosurgical generator, return electrode assembly 140 is able to function as the return electrode of surgical system 1000. Elongated shaft 310, more specifically, may be formed from steel or cast iron, for example, although other materials are also contemplated. Portions of elongated shaft 310 may be coated with an insulative coating such as, for example, chromium nitrile, epoxy, or silicon, to insulate a portion of elongated shaft 310, while leaving a portion exposed to enable electrical communication between return electrode assembly 140 and the exposed portions of elongated shaft 310, as detailed below. The insulative coating may be applied with a sprayer, brush, roller, via dipping, or via any other suitable method, and may define a thickness of between about 4 mm and about 6 mm (taking into account manufacturing tolerances of coating application). Further, the surface(s) to be coated may mechanically roughened and/or chemically etched to maximize bonding strength of the insulative coating thereon.

End effector assembly 320 of tenaculum 300 includes a pair of first and second jaw members 322, 324 and an opposed third jaw member 326. First and second jaw members 322, 324 are fixed relative to one another, disposed in similar orientation relative to one another, and spaced-apart from one another. Third jaw member 326 generally opposes first and second jaw members 322 and is aligned within the space defined between first and second jaw members 322, 324. First and second jaw members 322, 324 and/or third jaw member 326 are pivotable between a spaced-apart position, wherein third jaw member 326 is spaced-apart relative to first and second jaw members 322, 324, and a closed position, wherein third jaw member 326 is approximated relative to first and second jaw members 322, 324 and extends at least partially therebetween. Jaw members 322, 324, 326 may define hooked distal ends 323, 325, 327, respectively, to facilitate grasping tissue, although other configurations are also contemplated. The actuator of tenaculum 300 is configured to move the movable jaw member(s), e.g., jaw members 322, 324, between the open and closed positions.

Some or all of the jaw members 322, 324, 326 may be formed from an electrically-conductive material, e.g., steel or cast iron, and may be partially or wholly coated with an insulative coating, similarly as detailed above with respect to elongated shaft 310. Coating at least a portion of jaw members 322, 324, and/or 326 with an insulative material inhibits electrical coupling with active electrode assembly 140 of energy-based surgical device 100.

The space between jaw members 322, 324 combined with the rounded end configurations of the jaw members, particularly that of the movable jaw members, e.g., jaw member 322, 324, helps reduce the force needed to close the jaw members 322, 324, 326 about tissue that may be thicker than the minimum spacing between the jaw members 322, 324 and 326 in the closed position. This ability to completely close the jaw members 322, 324, 326 assures the jaw members 322, 324, 326 may pass into and through the lumen 126 of energy-based surgical device 100 without causing physical or electrical damage to the interior of energy-based surgical device 100.

The hooked distal ends 323, 325, 327 of jaw members 322, 324, 326, respectively, are configured to serve as tissue perforators, wherein the ends 323, 325 on jaw members 322, 324 overlap the end 327 of jaw member 326 in the closed position of jaw members, perforating tissue disposed therebetween. The ends 323, 325, 327 are substantially rounded and may define obtuse-cone shaped configurations. When the jaw members 322, 324, 326 are disposed in the closed position, the spaces between ends 323 and 327 and between ends 327 and 325 is at minimum approximately half the maximum diameter of the overlapped portions of the ends 323, 325, 327. These spaces and the substantially rounded configuration of the ends 323, 325, 327 facilitate maintaining a grip on tissue and perforating, without cutting through, the grasped tissue.

In embodiments where the system 1000 (FIG. 2) of the present disclosure is used with a specimen bag 1200 (FIG. 13), the jaw members 322, 324, 425 further provide the benefit of, and may be further configured to, inhibiting catching on the specimen bag 1200 while being inserted and, due to the fact that the ends 323, 325, 327 are radiused, e.g., defining obtuse cones, the ends 323, 325, 327 are substantially incapable of perforating the specimen bag 1200.

Turning to FIGS. 1-8, as noted above, energy-based surgical device 100 generally includes proximal hub 110, elongated outer tube 120, active electrode assembly 130, and return electrode assembly 140. Referring to FIGS. 1 and 3-5, proximal hub 110 includes a base 112, a seal 114, and a cap 116 and defines a lumen 118 extending longitudinally therethrough. Base 112 of proximal hub 110 is fixedly engaged about proximal end portion 122 of elongated outer tube 120 such that lumen 118 of proximal hub 110 and lumen 126 of elongated outer tube 120 are aligned with one another.

Seal 114 of proximal hub 110 is disposed within base 112. Cap 116 defines internal threads 117 and base 112 defines external threads 113 to enable cap 116 to be releasably screwed onto base 112, thereby retaining seal 114 within lumen 118 of proximal hub 110 between cap 116 and base 112. Seal 114 may be configured to establish a seal about instrumentation inserted through proximal hub 110, e.g., obturator 200 or tenaculum 300, and/or to seal lumen 118 in the absence of instrumentation inserted through proximal hub 110.

With reference to FIGS. 1, 3, and 6-8, elongated outer tube 120 of energy-based surgical device 100 includes proximal end portion 122, a distal end portion 124, and lumen 126 extending longitudinally therethrough. Elongated outer tube 120 is formed from or coated (partially or fully) with an electrically-insulative material or is otherwise configured to be electrically isolated from tenaculum 300 (FIG. 2) and from active and return electrode assemblies 130, 140, respectively. Elongated outer tube 120 further includes a slot 128a defined therethrough at a position proximally-spaced from distal end portion 124, a pair of spaced-apart rivet apertures 128b longitudinally aligned with one another and positioned between slot 128a and distal end portion 124 of elongated outer tube 120, a distal overhang 128c extending distally from a distal end portion 124 of elongated outer tube 120 in alignment with slot 128a and apertures 128b, and three cut-outs 128d defined about the annular perimeter of distal edge 125 of distal end portion 124 of elongated outer tube 120. Distal overhang 128c and cut-outs 128d are equally-spaced about the annular perimeter of distal edge 125.

Referring still to FIGS. 1, 3, and 6-8, active electrode assembly 130 of energy-based surgical device 100 includes a distal cutting member 132 and a pair of flat conductors 134. Distal cutting member 132 is formed at least partially from an electrically-conductive material, e.g., brass, is fixedly engaged at distal end portion 124 of elongated outer tube 120, and defines a U-shaped configuration including a U-shaped distal cutting edge 133a and a mouth 133b. The inwardly-facing circumferential portion of distal cutting member 132 may be coated with an insulative material such as, for example, chromium nitrile, epoxy, or silicon, and may be applied and/or define a thickness similarly as detailed above. This insulative coating inhibits electrical contact between distal cutting member 132 and, for example, tenaculum 300 (see FIG. 2). Distal cutting member 132 further includes three circumferentially-spaced protrusions 133c extending proximally therefrom. Protrusions 133c are shaped complementary to cut-outs 128d of distal edge 125 of distal end portion 124 of elongated outer tube 120 to enable receipt of protrusions 133c within cut-outs 128d to facilitate engagement of distal cutting member 132 with elongated outer tube 120. Mouth 133b and protrusions 133c are equally-spaced about the annular perimeter of distal cutting member 132 such that, when distal cutting member 132 is engaged at distal end portion 124 of elongated outer tube 120 (with protrusions 133c received within cut-outs 128d), distal overhand 128c of elongated outer tube 120 extends through mouth 133b of active electrode assembly 130.

As noted above, distal cutting edge 133a of distal cutting member 132 defines a U-shaped configuration to enable tissue cutting about a U-shaped arc. As a result thereof, coring of tissue, which may occur with a full or near-full circumference cutting arm, is inhibited. Rather, an elongated strip of tissue is cut, as detailed below. With particular reference to FIG. 7, distal cutting edge 133a defines, in embodiments, an angle "α" of between about 10 degrees and about 30 degrees, in embodiments, of between about 15 and about 25 degrees, and, in embodiments, of about 20 degrees (the "about" taking into account manufacturing tolerances and other variations). Distal cutting edge 133a further defines concave (as viewed from the distal end) upright portions 133d. The concave configuration of upright portions 133d helps ensure tenaculum 300 does not contact distal cutting edge 133a of distal cutting member 132.

Referring to FIGS. 1-3, 6, and 8, flat conductors 134 are electrically-conductive, e.g., formed from an electrically-conductive foil, e.g., brass foil, or other suitable material, and extend along the exterior surface of elongated outer tube 120 on opposed sides thereof. Elongated outer tube 120 and flat conductors 134 may together be surrounded via an electrically-insulative shrink wrap or other suitable coating during manufacture such that flat conductors 134 are not exposed along the length of elongated outer tube 120. For example, the insulative coating may be chromium nitrile, epoxy, or silicon.

Flat conductors 134 are further configured for mating contact with distal cutting member 132, e.g., distal cutting member 132 is configured for positioning about distal portions of flat conductors 134 in mating contact with the exterior surfaces thereof upon engagement of distal cutting member 132 with elongated outer tube 120, or distal portions of flat conductors 134 may be configured to surround the exterior surface of distal cutting member 132 in mating contact therewith. The proximal end portions of flat conductors 134 are configured to connect to the electrosurgical generator, e.g., via lead wires (not shown) extending through an electrosurgical cable (not shown), to enable the supply of electrosurgical energy to distal cutting member 132 upon activation such that distal cutting member 132 may function as the active electrode.

With reference to FIGS. 1, 3 and 4-8, return electrode assembly 140 of energy-based surgical device 100 includes a flat spring 142 and a pair of rivets 143. Flat spring 142 is formed from an electrically-conductive material, e.g., phosphor-bronze, beryllium copper, or other suitable material, and is aligned with both slot 128a and distal overhang 128c of elongated outer tube 120. Flat spring 142 is further aligned with open distal mouth 136 of distal cutting member 132 such that flat spring 142 extends through mouth 136 without contacting distal cutting member 132. Flat spring 142 is advantageous at least in that, in embodiments, the length of tissue in the direct line of communication between distal cutting member 132 and flat spring 142 is of relatively constant length. Flat spring 142 further ensures contact quality with tenaculum 300 and tissue passing through energy-based surgical device 100, thus ensuring appropriate conduction of energy to cut tissue. Outwardly-facing portions of flat spring 142, e.g., head 144 of flat spring 142, may be coated with an insulative material, similarly as detailed above.

Flat spring 142 includes a head 144, a belly 146 extending proximally from head 144, and a foot 148 extending proximally from belly 146. Head 144 includes a flat top 145a defining a free proximal end 145b and extending distally from free proximal end 145b along the exterior surface of elongated outer tube 120 and distal overhang 128c thereof. Flat top 145a is secured to the exterior surface of elongated outer tube 120 via rivets 143, which extend through spaced-apart rivet apertures 145c defined through flat top 145a and spaced-apart rivet apertures 128b defined through elongated outer tube 120. Head 144 bends around the free end of distal overhand 128a of elongated outer tube 120. More specifically, a face 145d of head 144 includes a first end that depends from distal end portion 145e of flat top 145a and distal overhand 128c of elongated outer tube 120 in generally perpendicular orientation relative thereto such that face 145d covers a portion of lumen 126 of elongated outer tube 120 and defines a distally-facing surface.

Belly 146 extends proximally from a second, opposite end of face 145d in generally perpendicular orientation relative thereto. Belly 146, more specifically, extends proximally from the second, opposite end of face 145d through open distal mouth 136 of distal cutting member 132 and into lumen 126 of elongated outer tube 120. Belly 146 extends through a portion of lumen 126 of elongated outer tube 120 and defines an arcuate configuration with a concave surface 147a facing flat top 145a of head 144 and a convex surface 147b facing in an opposite direction. In an at-rest position, belly 146 (see FIG. 5) traverses the full diameter of lumen 126 of elongated outer tube 120, a substantial portion thereof (e.g., greater than 75% of the diameter thereof), or a majority thereof (e.g., greater than 50% of the diameter thereof).

Belly 146 is resiliently flexible upon sufficient urging, e.g., in response to insertion of tenaculum 300 through lumen 126 of elongated outer tube 120, such that belly 146 is displaced towards flat top 145a of head 144 to provide sufficient clearance for insertion of instrumentation, e.g., obturator 200 (see FIGS. 9 and 10) or tenaculum 300 (see FIGS. 11 and 12), through lumen 126 of elongated outer tube 120. The resilient flexibility of belly 146 ensures that, with tenaculum 300 inserted through lumen 126, belly 146 is maintained in contact, under bias, with the exterior surface of elongated shaft 310 of tenaculum 300, thus ensuring electrical continuity therebetween.

Foot 148 of flat spring 142 defines a step 149a and a flat free end portion 149b. Step 149a extends proximally from the proximal end portion of belly 146 and is configured to extend through slot 128a of elongated outer tube 120 from the interior thereof to the exterior thereof. Flat free end portion 149b extends proximally from step 149a along the exterior of elongated outer tube 120. Foot 148 is coupled to elongated outer tube 120 via the interaction of step 149a with slot 128a; however, this coupling still enables belly 146 to resiliently flex, as detailed above, to permit passage of obturator 200 (see FIGS. 9 and 10) or tenaculum 300 (see FIGS. 11 and 12) through elongated outer tube 120. Flat free end portion 149b may further be coupled to elongated outer tube 120 via a rivet-and-slot coupling (not shown) so as to engage flat free end portion 149b to elongated outer tube 120 while still permitting motion of belly 146, as detailed above.

Referring to FIGS. 9-10, as noted above, obturator 200 is insertable through lumen 126 of elongated outer tube 120 of energy-based surgical device 100 to a fully inserted position, wherein proximal collar 220 of obturator 200 abuts or is disposed in close proximity to proximal hub 110 of energy-based surgical device 100 and distal end portion 214 of obturator 200 protrudes distally from energy-based surgical device 100. Upon insertion of obturator 200 through lumen 126, more specifically, belly 146 of return electrode assembly 140 of energy-based surgical device 100 is slid through mouth 236 of channel 230 of obturator 200, into and along distal portion 238a of channel 230 and, ultimately, into body portion 238b of channel 230. In this manner, once obturator 200 reaches the fully-inserted position, belly 146 of return electrode assembly 140 is received within channel 230. With belly 146 received within channel 230, less flexion of belly 146 is required to permit obturator 200 to extend through elongated outer tube 120 of energy-based surgical device 100.

With reference to FIGS. 11 and 12, as also noted above, with tenaculum 300 inserted through energy-based surgical device 100, end effector assembly 320 extends distally from energy-based surgical device 100 while the actuator of tenaculum 300 remains proximally-disposed relative to energy-based surgical device 100. As tenaculum 300 is inserted through energy-based surgical device 100, elongated shaft 310 is urged into and resiliently flexes belly 146 of return electrode assembly 140 out of the way to enable passage of tenaculum 300 through elongated outer tube 120 of energy-based surgical device 100. As a result, belly 146 is maintained in contact, under bias, with the exterior surface of elongated shaft 310 of tenaculum 300, thus ensuring electrical continuity. Head 144 and/or foot 148 may also be flexed in response to insertion of tenaculum 300 through elongated outer tube 120 of energy-based surgical device 100 to accommodate tenaculum 300. With tenaculum 300 inserted through energy-based surgical device 100, effector assembly 320 thereof protrudes from elongated outer tuber 120, distal cutting member 132 of active electrode assembly 130, and head 144 of return electrode assembly 140 such that jaw members 322, 324, 326 may be manipulated to grasp tissue.

Figure 13:
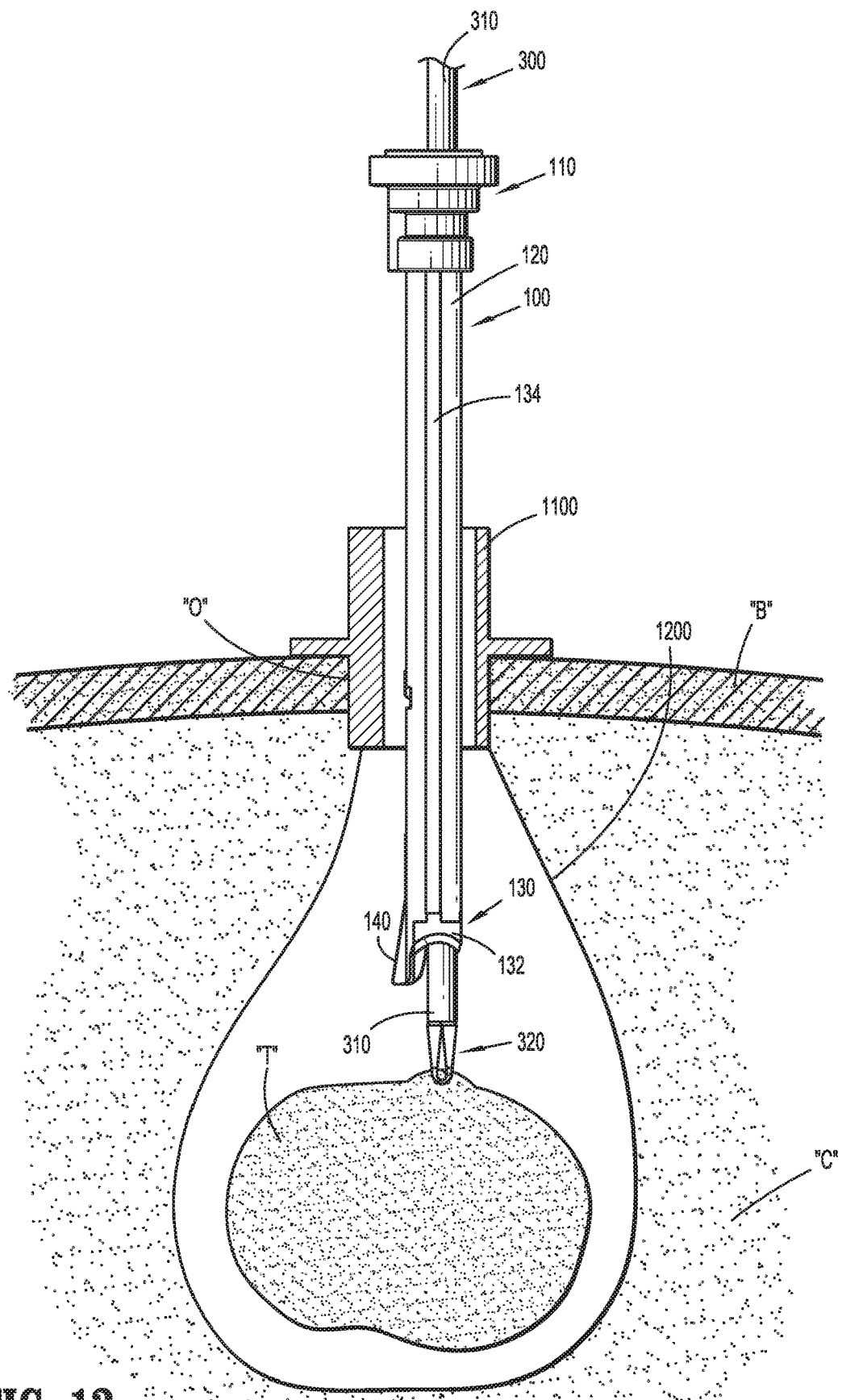
FIGS. 13-15 are longitudinal, cross-sectional views illustrating use of the energy-based surgical device of FIG. 1 and the tenaculum of FIG. 2 to break down and remove a tissue disposed within a specimen bag in an internal body cavity.
Figure 14:
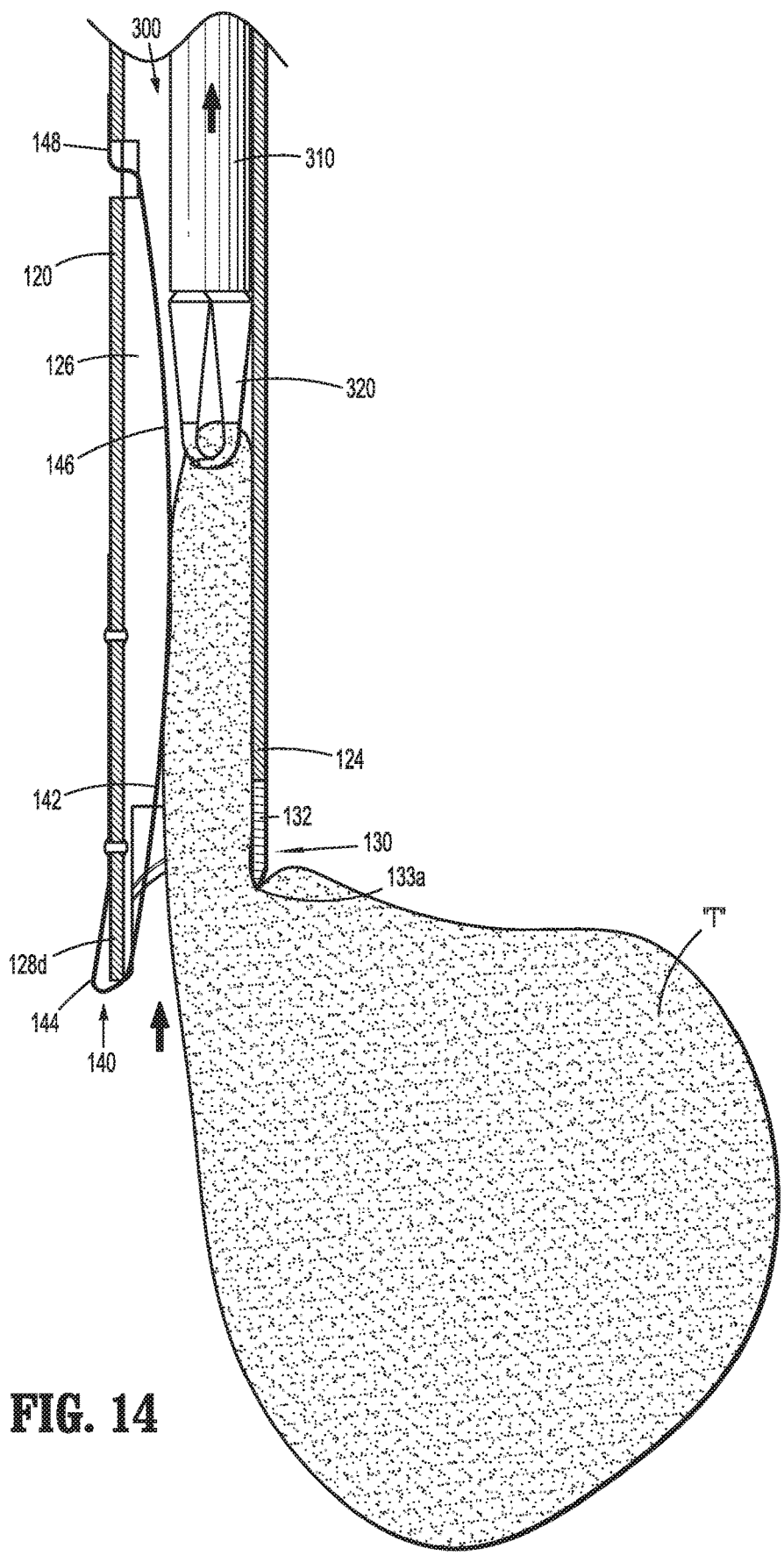
Figure 15:
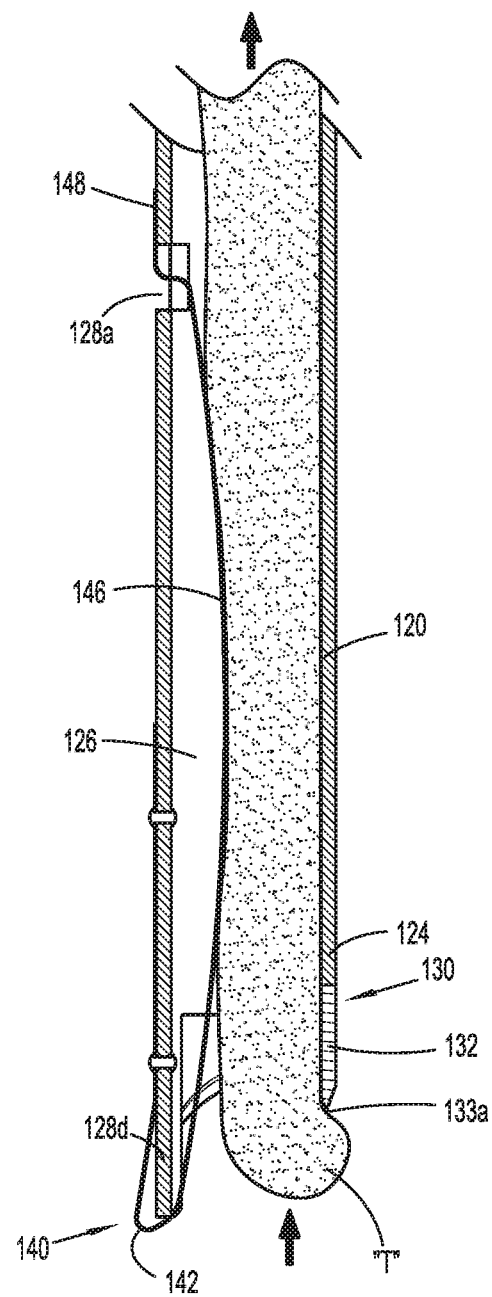

Turning to FIGS. 13-15, in conjunction with FIG. 2, the use of surgical system 1000 is described. Although detailed below for use in conjunction with an access port 1100 and specimen bag 1200, surgical system 1000 may be configured for use with other suitable instrumentation to facilitate breakdown and removal of tissue from an internal body cavity.

Initially, with reference to FIG. 13, access port 1100 is disposed within an opening "O" (naturally occurring or surgically created) through the body "B" to provide access to an internal body cavity "C." Specimen bag 1200 may be extended through or about access port 1100. Tissue "T" to be broken down and removed may be surrounded by or otherwise moved into specimen bag 1200 so as to isolate tissue "T" from the internal body cavity "C."

With tissue "T" to be removed disposed within specimen bag 1200 and isolated from the internal body cavity "C," obturator 200 may be inserted through energy-based surgical device 100 (see FIGS. 2, 9, and 10) and energy-based surgical device 100, together with obturator 200, may be inserted through access port 1100 and into specimen bag 1200 within the internal body cavity "C." Obturator 200 facilitates atraumatic insertion of energy-based surgical device 100 and inhibits damage to access port 1100, specimen bag 1200, and/or other instrumentation during such insertion. Once energy-based surgical device 100 is properly inserted and positioned, obturator 200 may be removed.

Referring to FIG. 13, once obturator 200 (FIG. 2) has been removed, tenaculum 300 may be inserted through energy-based surgical device 100 and into specimen bag 1200 adjacent tissue "T." End effector assembly 320 of tenaculum 300 may then be manipulated and/or actuated to grasp tissue "T" between jaw members 322, 324, 326.

With additional reference to FIGS. 14 and 15, once tissue "T" is grasped by jaw members 322, 324, 326 of end effector assembly 320 of tenaculum 300, system 1000 may be activated, e.g., via activating a footswitch, handswitch, or other suitable activator (not shown). Upon activation of system 1000, electrosurgical energy is delivered from the electrosurgical generator (e.g., via one or more electrosurgical cables including lead wires extending therethrough) to flat conductors 324 and, ultimately, to distal cutting member 322.

Once system 1000 is activated, tenaculum 300 is drawn proximally through elongated outer tube 120 of energy-based surgical device 100 such that the grasped portion of tissue "T" is pulled proximally through distal cutting member 322 and into lumen 126 of elongated outer tube 120. As the grasped portion of tissue "T" is pulled in this manner, electrosurgical energy is delivered from U-shaped distal cutting edge 133*a* to tissue "T" to electromechanically cut tissue "T" into a strip to enable the strip of tissue "T" to be drawn proximally into lumen 126 and through elongated outer tube 120. As noted above, since distal cutting edge 133*a* defines a U-shaped (and not a full circumferential) configuration, coring of tissue "T" is inhibited. Rather, tissue "T" is cut into an increasingly-elongated strip. Further, due to the configuration of distal cutting edge 133*a*, detailed above, power is concentrated at distal cutting edge 133*a* to facilitate electromechanical tissue cutting as tissue "T" is drawn through distal cutting member 132 and into elongated outer tube 120.

Electrosurgical energy is conducted from distal cutting edge 133*a*, through tissue "T," to flat spring 142 of return electrode assembly 140. Flat spring 142 is disposed in close proximity with distal cutting edge 133*a* and is flexed away from distal cutting edge 133*a* only sufficiently so as to enable passage of tenaculum 300 and tissue "T" into elongated outer tube 120. Thus, flat spring 142 is maintained in close proximity to distal cutting edge 133*a* which also helps to facilitate electromechanical tissue cutting. The bias of flat spring 142 also maintains tension on tissue adjacent distal cutting edge 133*a*, which additionally facilitates electromechanical tissue cutting.

Electrosurgical energy is returned to the electrosurgical generator from flat spring 142 via elongated shaft 310 of tenaculum 300 (and an electrosurgical cable including a lead wire extending between elongated shaft 310 and the electrosurgical generator). Belly 146 of flat spring 142, as detailed above, is biased into contact with elongated shaft 310, thus maintaining electrical continuity through the return path to enable the return of electrosurgical energy to the electrosurgical generator. However, other alternate or additional conductors (not shown) may be provided to enable return of electrosurgical energy in the absence of contact between flat spring 142 and tenaculum 300 or in addition thereto.

As tissue "T" is cut into an elongated strip, as detailed above, and pulled through elongated outer tube 120 of energy-based surgical device 100, the remainder of tissue "T" may roll or rotate relative to energy-based surgical device 100 such that the strip of tissue "T" is skived from the outer circumferential surface of tissue "T" like a ball of yarn unraveling. Tissue "T" may be fully cut into a single elongated strip and removed using tenaculum 300, or may be reduced to a sufficiently small size so as to enable removal of tissue "T" along with the removal of specimen bag 1200.

Referring back to FIG. 2, generally, surgical system 1000 may be configured for use with a robotic surgical system (not shown) configured to selectively manipulate energy-based surgical device 100, obturator 200, and/or tenaculum 300 as detailed above. The robotic surgical system, as detailed below, employs various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An energy-based surgical device, comprising:
an elongated outer tube defining a distal end portion, a proximal end portion, and a lumen extending longitudinally therethrough, the elongated outer tube including a distal overhang extending distally therefrom;
a proximal hub disposed at the proximal end portion of the elongated outer tube;
a distal cutting member disposed at the distal end of the elongated outer tube, the distal cutting member having a U-shaped cutting edge and defining a mouth, wherein the distal overhang extends through the mouth; and
a flat spring aligned with the distal overhang, the flat spring including a first portion extending distally along an exterior surface of the elongated outer tube and the distal overhang, a second portion extending from the first portion and bent over a free distal end of the distal overhang, and a third portion extending from the second portion proximally through the mouth of the distal cutting member and into the lumen of the elongated outer tube, the third portion of the flat spring traversing a majority of a diameter of the lumen of the elongated outer tube,
wherein the distal cutting member and the flat spring are adapted to connect to a source for electrosurgical energy for conducting bipolar energy through tissue disposed therebetween to cut tissue.

2. The energy-based surgical device according to claim 1, wherein the third portion of the flat spring traverse at least 75% of a diameter of the lumen of the elongated outer tube.

3. The energy-based surgical device according to claim 1, wherein the third portion of the flat spring traverses an entirety of a diameter of the lumen of the elongated outer tube.

4. The energy-based surgical device according to claim 1, wherein the third portion of the flat spring is resiliently flexible to permit insertion of an instrument through the elongated outer tube.

5. The energy-based surgical device according to claim 1, wherein the flat spring includes a fourth portion extending from the third portion, the forth portion extending from the lumen of the elongated outer tube, through a slot defined within the elongated outer tube, to an exterior of the elongated outer tube.

6. The energy-based surgical device according to claim 1, wherein the second portion of the flat spring includes a face covering a portion of the lumen and oriented in a distally-facing direction.

7. The energy-based surgical device according to claim 1, wherein the U-shaped cutting edge of the distal cutting member defines an edge angle of from about 10 degrees to about 30 degrees.

8. The energy-based surgical device according to claim 1, wherein uprights of the U-shaped cutting edge are concave.

9. The energy-based surgical device according to claim 1, wherein the proximal hub includes a seal disposed therein configured to sealingly engage an instrument inserted therethrough.

10. The energy-based surgical device according to claim 1, further comprising at least one flat conductor extending along the exterior surface of the elongated outer tube, the at least one flat conductor electrically coupled to the distal cutting member and adapted to connect to a source of electrosurgical energy to supply electrosurgical energy to the distal cutting member.

11. A surgical system, comprising:
an energy-based surgical device, including:
an elongated outer tube defining a distal end portion, a proximal end portion, and a lumen extending longitudinally therethrough;
a proximal hub disposed at the proximal end portion of the elongated outer tube;
a distal cutting member disposed at the distal end of the elongated outer tube, the distal cutting member adapted to connect to a source for electrosurgical energy for applying electrosurgical energy to tissue; and
a resiliently flexible flat spring including a portion extending proximally into the lumen of the elongated outer tube and occupying a portion of an inner diameter of the elongated outer tube to define a reduced clearance through the elongated outer tube;
a tenaculum including an elongated shaft and an end effector assembly disposed at a distal end portion of the elongated shaft, the elongated shaft having an outer diameter less than the inner diameter of the elongated outer tube and greater than the reduced clearance, the elongated shaft formed at least partially from an electrically-conductive material and adapted to connect to a source of electrosurgical energy, wherein the tenaculum is configured for insertion through the lumen of the elongated outer tube whereby, due to the elongated shaft of the tenaculum having a diameter greater than the reduced clearance, the elongated shaft of the tenaculum displaces the portion of the flat spring such that the portion of the flat spring is biased into contact with the elongated shaft of the tenaculum to establish electrical continuity therebetween to define a return path for the electrosurgical energy; and
an obturator configured for insertion through the lumen of the elongated outer tube, wherein the obturator defines a channel configured to at least partially receive the portion of the flat spring therein when the obturator is inserted through the lumen of the elongated outer tube.

12. The surgical system according to claim 11, wherein the end effector assembly of the tenaculum incudes at least two pivotable jaw members configured to pivot relative to one another to grasp tissue.

13. The surgical system according to claim 11, wherein the distal cutting member of the energy-based surgical device includes a U-shaped cutting edge defining a mouth, and wherein the flat spring extends through the mouth.

14. The surgical system according to claim 11, wherein the flat spring extends proximally along an exterior surface of the elongated outer tube and bends around the distal end portion of the elongated outer tube before extending proximally into the lumen of the elongated outer tube.

15. The surgical system according to claim 11, wherein the portion of the flat spring traverses a majority of a diameter of the lumen of the elongated outer tube.

16. The surgical system according to claim 11, wherein the portion of the flat spring traverses a substantial portion of a diameter of the lumen of the elongated outer tube.

17. The surgical system according to claim 11, wherein the proximal hub includes a seal disposed therein configured to sealingly engage the elongated shaft of the tenaculum when the tenaculum is inserted through the lumen of the elongated outer tube.

18. An energy-based surgical device, comprising:

an elongated outer tube defining a distal end portion, a proximal end portion, and a lumen extending longitudinally therethrough, the elongated outer tube including a distal overhang extending distally therefrom;

a distal cutting member disposed at the distal end of the elongated outer tube, the distal cutting member being non-continuous about the distal end portion of the outer tube, having a U-shaped cutting edge, and defining a mouth, wherein the distal overhang extends through the mouth;

a flat spring aligned with the distal overhang, the flat spring including a first portion extending from the distal overhang, through the mouth of the distal cutting member and into the lumen of the elongated outer tube, a portion of the flat spring traversing a majority of a diameter of the lumen of the elongated outer tube, wherein the distal cutting member and the flat spring are adapted to connect to a source for electrosurgical energy for conducting bipolar energy through tissue disposed therebetween to cut tissue.

* * * * *